(12) United States Patent
Pitigoi-Aron et al.

(10) Patent No.: US 9,436,270 B2
(45) Date of Patent: Sep. 6, 2016

(54) WIRELESS LOW-ENERGY SECURE DATA TRANSFER

(71) Applicant: QUALCOMM Incorporated, San Diego, CA (US)

(72) Inventors: Radu Pitigoi-Aron, San Jose, CA (US); Justin Patrick McGloin, Los Altos, CA (US)

(73) Assignee: QUALCOMM INCORPORATED, San Diego, CA (US)

( * ) Notice: Subject to any disclaimer, the term of this patent is extended or adjusted under 35 U.S.C. 154(b) by 106 days.

(21) Appl. No.: 14/179,259

(22) Filed: Feb. 12, 2014

(65) Prior Publication Data

US 2015/0227191 A1 Aug. 13, 2015

(51) Int. Cl.

| | |
|---|---|
| *G06F 21/00* | (2013.01) |
| *H04L 29/06* | (2006.01) |
| *G06F 1/32* | (2006.01) |
| *G06F 21/72* | (2013.01) |
| *G06F 19/00* | (2011.01) |
| *H04W 4/00* | (2009.01) |
| *H04W 12/06* | (2009.01) |
| *H04W 84/18* | (2009.01) |

(Continued)

(52) U.S. Cl.
CPC ........... *G06F 1/3293* (2013.01); *A61B 5/0024* (2013.01); *G06F 19/3418* (2013.01); *G06F 21/72* (2013.01); *H04L 63/0861* (2013.01); *H04L 67/12* (2013.01); *H04W 4/008* (2013.01); *H04W 12/06* (2013.01); *H04W 84/18* (2013.01); *A61B 5/1118* (2013.01); *G06F 19/3406* (2013.01); *Y02B 60/50* (2013.01)

(58) Field of Classification Search
CPC .. G06F 1/3293; G06F 19/3418; G06F 21/72; H04W 12/06; H04W 4/008; H04W 84/18; A61B 5/002; H04L 63/0861; H04L 67/12
See application file for complete search history.

(56) References Cited

U.S. PATENT DOCUMENTS

| 8,531,291 B2 | 9/2013 | Tran | |
|---|---|---|---|
| 2003/0051050 A1* | 3/2003 | Adelaide et al. | 709/238 |

(Continued)

FOREIGN PATENT DOCUMENTS

| WO | WO-2004084720 A2 | 10/2004 |
|---|---|---|
| WO | WO-2006102538 A2 | 9/2006 |
| WO | WO-2009075457 A1 | 6/2009 |

OTHER PUBLICATIONS

Menezes, V., et al.,"Handbook of Applied Cryptography", 1997, CRC Press LLC, USA, 16 pages.

(Continued)

*Primary Examiner* — Lisa Lewis
(74) *Attorney, Agent, or Firm* — Kilpatrick Townsend & Stockton LLP

(57) ABSTRACT

Embodiments of the invention provide for a sensor system with enhanced low-power features. Embodiments can include transmission of sensor data from a transmitter unit to a receiver unit. The sensor data can flag the sensor data with a particular header ID, enabling the receiver unit to route the sensor data to a low-power processing unit within the receiver unit without using the receiver unit's higher-power application processer. Embodiments can also utilize a proprietary encryption engine to provide a supplementary encryption layer to any encryption utilized in the wireless protocol. The transmitter unit can also compress and batch the sensor data for sending, to further increase power savings.

30 Claims, 8 Drawing Sheets

(51) Int. Cl.
*H04L 29/08* (2006.01)
*A61B 5/00* (2006.01)
*A61B 5/11* (2006.01)

(56) References Cited

U.S. PATENT DOCUMENTS

| | | |
|---|---|---|
| 2006/0143439 A1* | 6/2006 | Arumugam et al. ......... 713/153 |
| 2007/0005388 A1* | 1/2007 | Busch et al. .................... 705/1 |
| 2007/0083717 A1* | 4/2007 | Rajamony et al. ........... 711/141 |
| 2008/0246629 A1 | 10/2008 | Tsui et al. |
| 2009/0058635 A1 | 3/2009 | Lalonde et al. |
| 2010/0138666 A1* | 6/2010 | Adams et al. ................ 713/186 |
| 2012/0100895 A1* | 4/2012 | Priyantha et al. ............ 455/574 |
| 2013/0138716 A1 | 5/2013 | Macwan et al. |
| 2013/0252543 A1* | 9/2013 | Badi et al. .................... 455/41.1 |
| 2014/0164700 A1* | 6/2014 | Liang ............................ 711/119 |
| 2014/0164725 A1* | 6/2014 | Jang et al. .................... 711/163 |
| 2014/0177494 A1* | 6/2014 | Min et al. ...................... 370/311 |
| 2014/0298341 A1* | 10/2014 | Duftler et al. ................ 718/100 |

OTHER PUBLICATIONS

International Search Report and Written Opinion—PCT/US2015/013107—ISA/EPO—Apr. 22, 2015.

* cited by examiner

WIRELESS LOW-ENERGY SECURE DATA TRANSFER

BACKGROUND

Advances in signal processing and component miniaturization have made possible the usage of wearable sensors for medical and/or physiological applications, such as monitoring heart rate, brain activity, and other body functions. These sensors can communicate sensor data wirelessly to a mobile device (e.g., smart phone, tablet, specialized device, etc.) for monitoring. Because these sensor systems are frequently on for large periods of time, power conservation and security are of particular importance.

SUMMARY

Embodiments of the invention provide for a sensor system with enhanced low-power features. Embodiments can include transmission of sensor data from at least one transmitter unit to a receiver unit. The sensor data can flag the sensor data with a particular header ID, enabling the receiver unit to route the sensor data to a low-power processing unit within the receiver unit without using the receiver unit's higher-power application processer. Embodiments can also utilize a proprietary encryption engine to provide a supplementary encryption layer to any encryption utilized in the wireless protocol. The transmitter unit can also compress and batch the sensor data for sending, to further increase power savings.

An example method of processing sensor data in a low-power wireless sensor interconnectivity system, according to the disclosure, includes receiving sensor data with a wireless communications interface of a mobile device, where the sensor data includes information indicative of data collected from one or more sensors, the mobile device includes an application processor and a low-power processor, and the sensor data is received while the application processor is in a low-power state. The method further includes determining a routing identifier associated with the sensor data, and based on the determined routing identifier, providing the sensor data to the low-power processing unit.

The example method can include one or more of the following features. The method can include decrypting the sensor data with the low-power processing unit using an encryption key and/or establishing the encryption key using biometric verification. The biometric verification can comprise using a scan of a fingerprint. The encryption key can be one of a plurality of predetermined encryption keys stored in a One Time Programmable (OTP) memory of the mobile device. The method can include writing a time stamp to an OTP memory regarding usage of the encryption key, decompressing the sensor data with the low-power processing unit, and/or sending the sensor data to a cloud-based decision support system (DSS).

An example apparatus in a low-power wireless sensor interconnectivity system, according to the disclosure, can include an application processor, a low-power processing unit, and a wireless communication interface communicatively coupled with the application processor and the low-power processing unit. The wireless communication interface can be configured to receive, while the application processor is in a low-power state, sensor data including information indicative of data collected from one or more sensors. The apparatus can further include one or more routing components communicatively coupled with the wireless communication interface and the low-power processing unit, where the one or more routing components are configured to determine a routing identifier associated with the sensor data and provide the sensor data to the low-power processing unit based on the determined routing identifier.

The example apparatus can include one or more of the following features. The low-power processing unit can be configured to decrypt the sensor data using an encryption key. The apparatus can include a biometric verification module configured to establish the encryption key using biometric verification. The biometric verification module can comprise a fingerprint scanner. The encryption key can be one of a plurality of predetermined encryption keys, the apparatus further comprising a One Time Programmable (OTP) memory of the apparatus configured to store the plurality of predetermined encryption keys. An OTP memory can be configured to store a time stamp regarding usage of the encryption key. The low-power processing unit can be configured to decompress the sensor data. Either or both the low-power processing unit or the application processor can be configured to send the sensor data to a cloud-based decision support system (DSS) via the wireless communication interface.

An example mobile device, according to the disclosure, can include means for receiving sensor data, where the means for receiving sensor data includes means for receiving information indicative of data collected from one or more sensors, and the means for receiving sensor data includes means for receiving the sensor data while an application processor of the mobile device is in a low-power state. The mobile device can further include means for determining a routing identifier associated with the sensor data, and means for providing the sensor data to a low-power processing unit based on the determined routing identifier.

The example mobile device can further include one or more of the following features. The mobile device can include means for decrypting the sensor data using an encryption key while the application processor of the mobile device is in the low-power state, and/or means for establishing the encryption key using biometric verification. The means for establishing the encryption key using biometric verification can include means for using a scan of a fingerprint. The encryption key can be one of a plurality of predetermined encryption keys, further comprising means for storing the plurality of predetermined encryption keys in a One Time Programmable (OTP) memory of the mobile device. The mobile device can include means for writing a time stamp to an OTP memory regarding usage of the encryption key, means for decompressing the sensor data while the application processor of the mobile device is in the low-power state, and/or means for sending the sensor data to a cloud-based decision support system (DSS).

An example non-transitory computer-readable medium, according to the disclosure, includes instructions for processing sensor data in a low-power wireless sensor interconnectivity system. The instructions include code for causing one or more components of a mobile device to perform functions including receiving sensor data with a wireless communications interface of the mobile device, where the code for receiving sensor data includes code for receiving information indicative of data collected from one or more sensors, and the code for receiving sensor data includes code for receiving the sensor data while an application processor of the mobile device is in a low-power state. The functions further include determining a routing identifier associated with the sensor data and providing the sensor data to a low-power processing unit based on the determined routing identifier.

The example computer-readable medium can further include one or more of the following features. The computer-readable medium can include code for decrypting the sensor data using an encryption key while the application processor of the mobile device is in the low-power state and/or establishing the encryption key using biometric verification. The encryption key can be one of a plurality of predetermined encryption keys, further comprising c for storing the plurality of predetermined encryption keys in a One Time Programmable (OTP) memory of the mobile device. The computer-readable medium can further include code for writing a time stamp to an OTP memory regarding usage of the encryption key and/or sending the sensor data to a cloud-based decision support system (DSS).

Items and/or techniques described herein may provide one or more of the following capabilities, as well as other capabilities not mentioned. Techniques can provide for increased power savings in the receiver unit by enabling the application processor to remain in a low-power ("sleep") state while the low-power processing unit processes sensor information. This can be used in conjunction with batching, compressing, and/or other power-saving techniques. Also, providing a supplementary encryption layer can provide additional security for sensitive information. These and other advantages and features are described in more detail in conjunction with the text below and attached figures.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
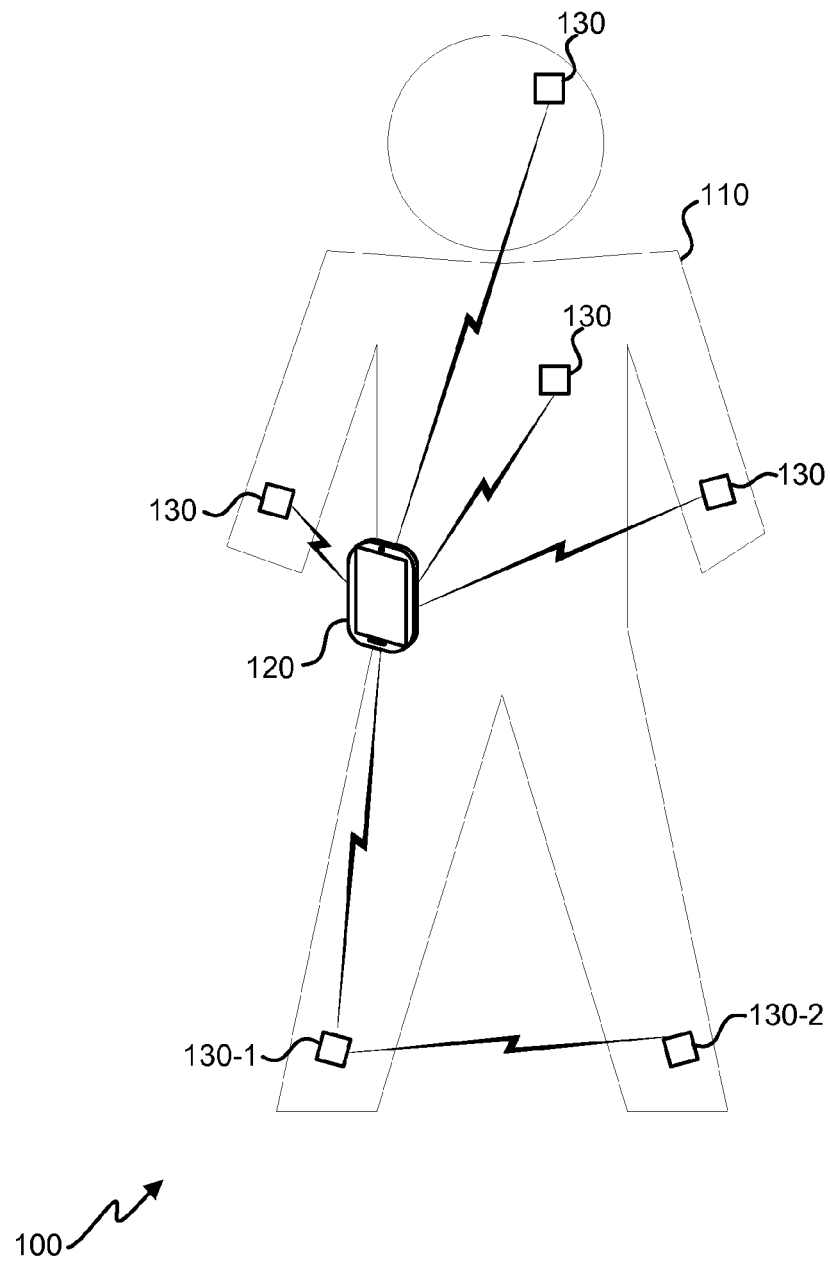
FIG. 1 is a simplified drawing illustrating an example sensor system, according to one embodiment.

The following description is provided with reference to the drawings, where like reference numerals are used to refer to like elements throughout. While various details of one or more techniques are described herein, other techniques are also possible. In some instances, structures and devices are shown in block diagram form in order to facilitate describing various techniques.

The usage of sensors in modern life is becoming more and more significant. The sensors cover almost every aspect of life, ranging from detecting and qualifying movements up and including monitoring vital parameters of human subjects. Today's technology allows for minuscule sensors, making them wearable; however there is still a need for energy to power the sensors and means to collect data. Most of the present implementations use either wired communications or assemblies with relatively large batteries. The power efficiency and the secure data transfer of these systems is particularly important for medical sensors systems, where the user must be comfortable and the system must work essentially continuously, with very short interruptions. Advances in signal processing and miniaturization have increased power efficiency, making possible the usage of the sensors for medical grade applications. Still, reduction in power consumption and secure data transfer, above and beyond current levels, are of primary importance in medical applications. Embodiments of the invention are directed toward addressing these major hurdles.

FIG. 1 is a simplified drawing illustrating an example sensor system 100, according to one embodiment. Here, the sensor system 100 comprises a plurality of transmitter units 130 wirelessly connected with a receiver unit 120. Transmitter units 130 can comprise one or more sensors configured to collect sensor data and transmit the sensor data to the receiver unit 120. The receiver unit 120 can process the sensor data, which can then be logged, transmitted to remote devices or systems, and/or used to trigger responsive measures and/or other actions.

In this example, the plurality of transmitter units of the sensor system 100 are worn by a user 110 and located at various locations on the user 110. In medical and other applications, the transmitter units 130 can be equipped and/or communicatively coupled with sensors configured to collect data regarding sound, light, pressure, motion, orientation, heat, and the like. This sensor data can then be used to determine temperature, pulse, muscle activity, brain activity, and/or other information regarding the health of the user 110. Depending on desired functionality, the sensor data transmitted by the transmitter units 130 can vary. The sensor data can include, for example, raw sensor data as received from the sensors, and/or it may include information derived therefrom.

The transmitter units 130 can be connected with the receiver unit 120 in a variety of ways to form different types of networks. For example, transmitter units 130 may each be communicatively coupled with the receiver unit 120 in a "hub and spoke" configuration where the transmitter units 130 are each in direct connection with the receiver unit 120. Additionally or alternatively, as shown in FIG. 1, one or more transmitter units 130-2 may communicate information to the receiver unit 120 via another transmitter unit 130-1. Various types of ad-hoc, mesh, and other wireless networking configurations may be used. Furthermore, although examples provided herein utilize Bluetooth™ (in particular, Bluetooth Low Energy (LE)), embodiments are not so limited. Additional or alternative wireless technologies may include other standards from the IEEE 802.15 body of standards, or even the 802 body of standards more broadly (802.11ah, for example), as well as others, depending on desired functionality The receiver unit 120 can also be worn by the user, and may comprise any of a variety of mobile devices. For example, the receiver unit 120 may comprise a tablet, mobile phone, media player, video gaming system, and the like. Additionally or alternatively, a receiver unit 120 may comprise proprietary hardware and/or software. With the sensor data received from the transmitter units 130, the receiver unit 120 can monitor and log information regarding the health of the user 110. Based on the information received, the receiver unit 120 may send certain information to one or more remote systems, such as a cloud-based decision support system (DSS), which can be maintained by the user's doctor, heath organization, third party support network, and the like. Depending on desired functionality this information may be sent via public and/or private data networks, including the Internet, using cellular, Wi-Fi, and/or other communication technologies, which may differ from the communication technology used to transmit the sensor data from the transmitter units 130 to the receiver unit 120.

Functionality of the sensor system 100 can by application and implementation. For example, the sensor system 100 may be used in a medical application to monitor the health of a user 110, such as the user's temperature, pulse, blood pressure, blood oxygen level, position, location, and the like. Sensor data (and/or data derived therefrom), may be logged by the receiver unit 120 for analysis by the user's doctor or other health professional. As indicated above, the data may be communicated by the receiver unit 120 to a remote system, such as a DSS, maintained by the user's doctor, a health organization, and the like. If sensor data indicates that the user 110 may be in a state of emergency, the receiver unit 120 may trigger other responses, such as contacting paramedics and/or other emergency response personnel to provide assistance to the user 110 (e.g., via a cellular or other wireless communication technology), alerting the user 110 (e.g., by sounding an alarm, vibrating, displaying a warning, etc.), or other such responses.

As indicated earlier, embodiments aren't limited to medical applications. Other health applications could utilize the sensor system 100 of FIG. 1, such as fitness applications, sports applications, and the like. Yet other embodiments could be implemented in applications outside medical or other health contexts, such as gaming, social media, security and the like. An example in a security context could include personal sensors used on doors or other possible entry ways, that would be always on and connected to a wireless device, similar to 120. The transfer can be encrypted, compressed, and/or batched, to save energy and prevent smart intruders for disabling or hacking the system.

Embodiments can include transmitter units 130 that utilize a certain header ID in some or all communications to the receiver unit 120, flagging the communications for low-power processing. Specialized hardware and/or software modules in the transmitter units 130 and receiver unit 120 can be utilized to implement this power-saving technique. Example embodiments are illustrated in FIGS. 2A-2C.

Figure 2A:
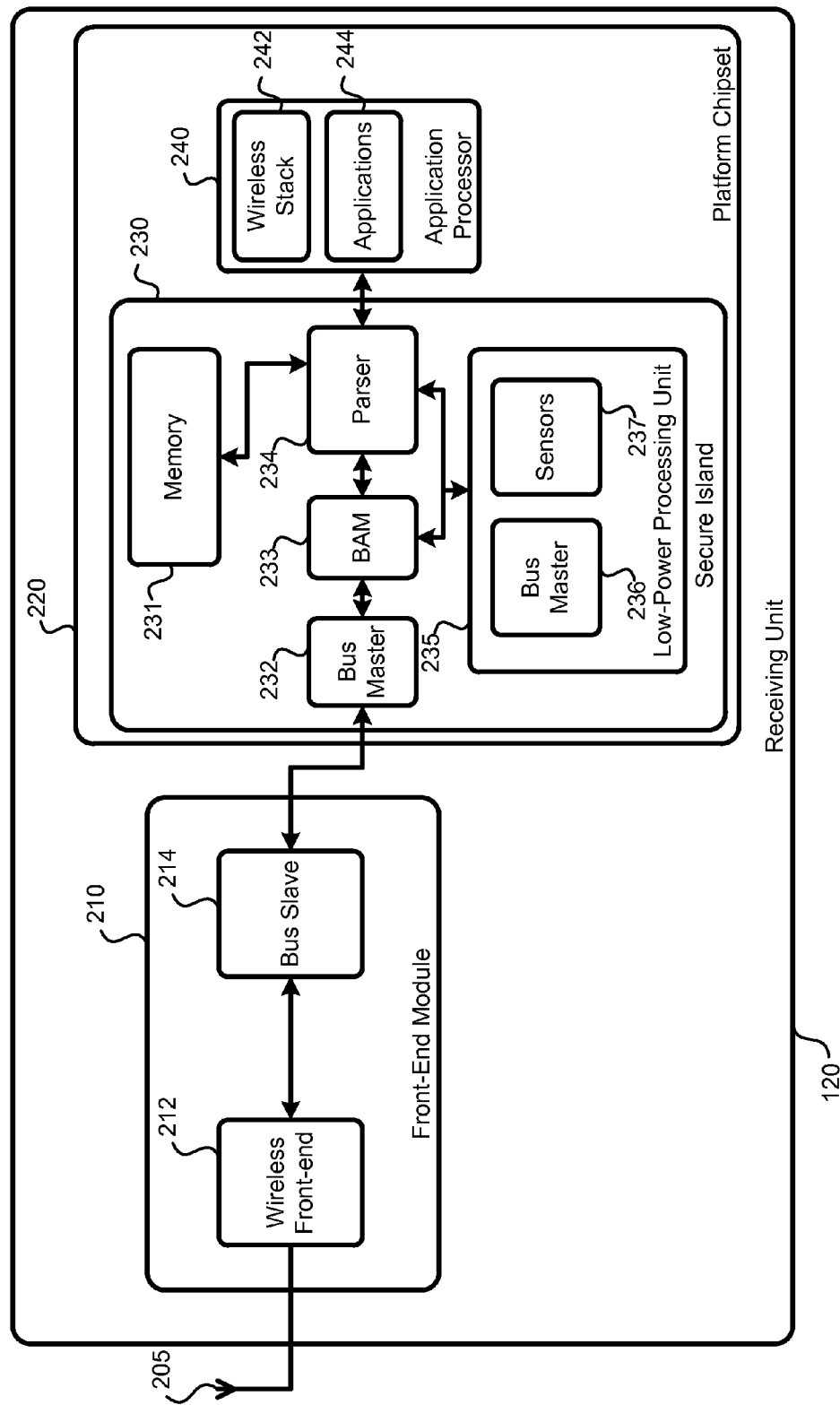
FIGS. 2A-2C are block diagrams of portions of a receiver unit adapted to implement power saving techniques discussed herein, according to one embodiment.
Figure 2B:
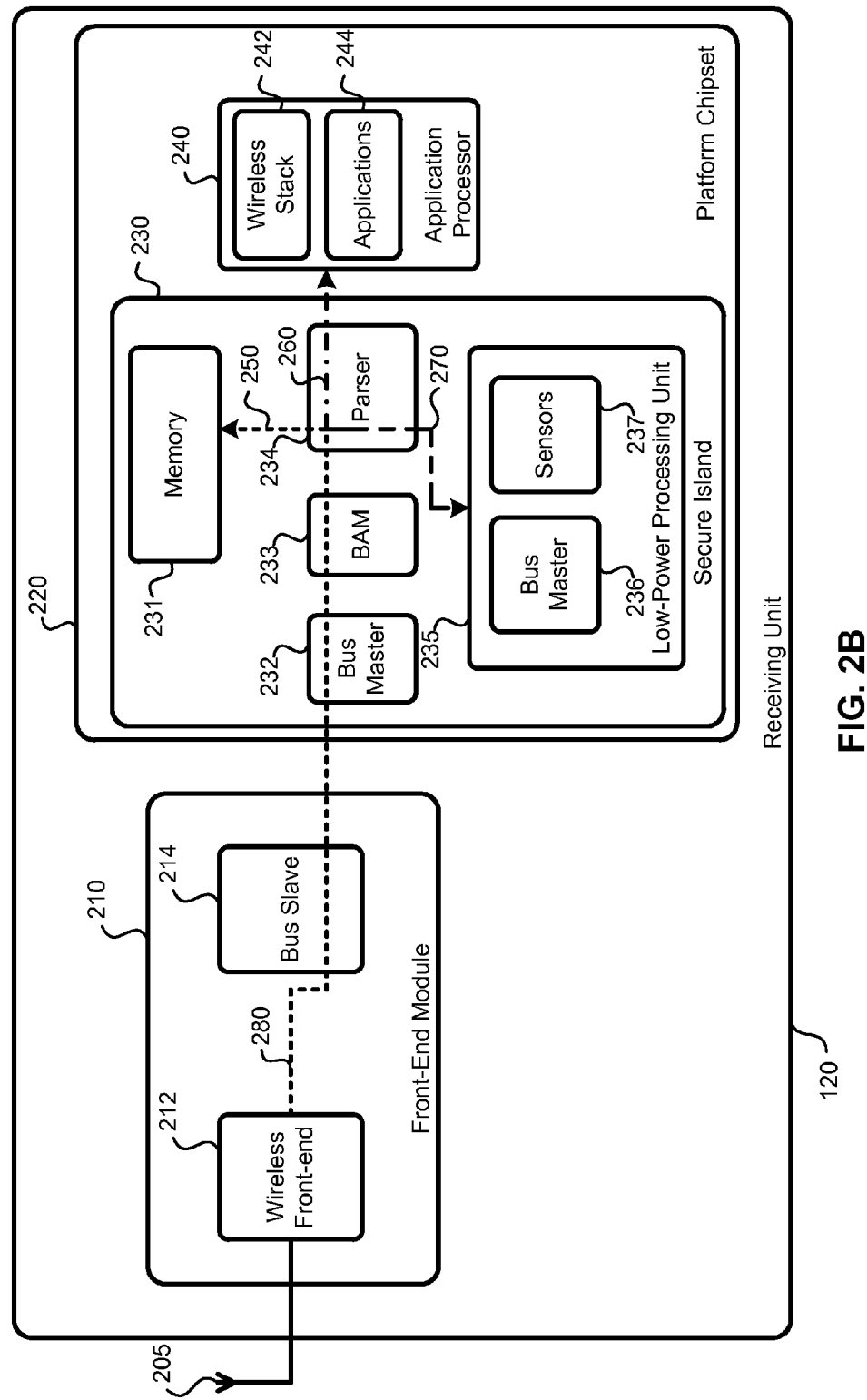
Figure 2C:
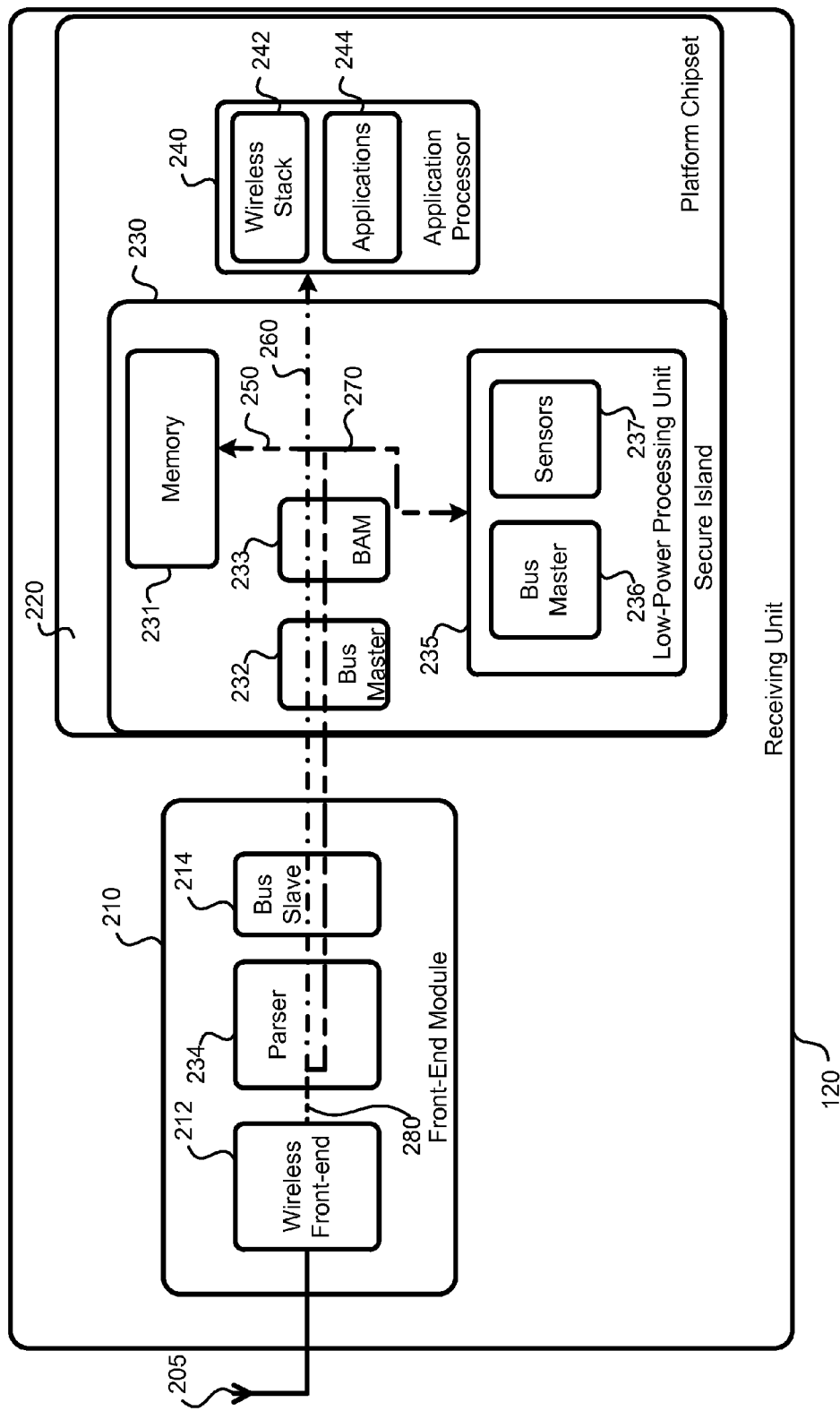

FIG. 2A is a block diagram of portions of a receiver unit 120 adapted to implement these power saving techniques, according to one embodiment. Components shown in FIG. 2A can be incorporated into hardware and/or software of a mobile or other electronic device, such as the mobile device discussed below in FIG. 6. FIG. 2A is provided as an example. It will be understood that components may be added, omitted, and/or substituted. A person of ordinary skill in the art will recognize many variations to the embodiment shown.

In FIG. 2A, the receiver unit 120 can receive sensor data (and/or other information) transmitted by transmitter units (130) at a front-end module 210 having a wireless front-end unit 212. A wireless front-end unit 212 can utilize a variety of wireless technologies, such as those previously discussed.

In one embodiment, for example, the wireless front-end may be capable of receiving Bluetooth Low Energy (LE) wireless signals. The wireless front-end unit 212 can receive wireless communication via an antenna 205.

The wireless front-end unit 212 can communicate received data to a bus slave 214. The bus slave can, in turn, communicate received data to other components of the receiver unit 120 via the bus. Different technologies may be used to implement the bus, according to desired functionality, manufacturing concerns, and/or other factors. In some embodiments, for example, the bus slave 214 can be communicatively coupled with a SLIMbus. Other bus technologies can include, for example, Universal Asynchronous Receiver/Transmitter (UART) or Inter-Integrated Circuit (I2C).

Figure 5:
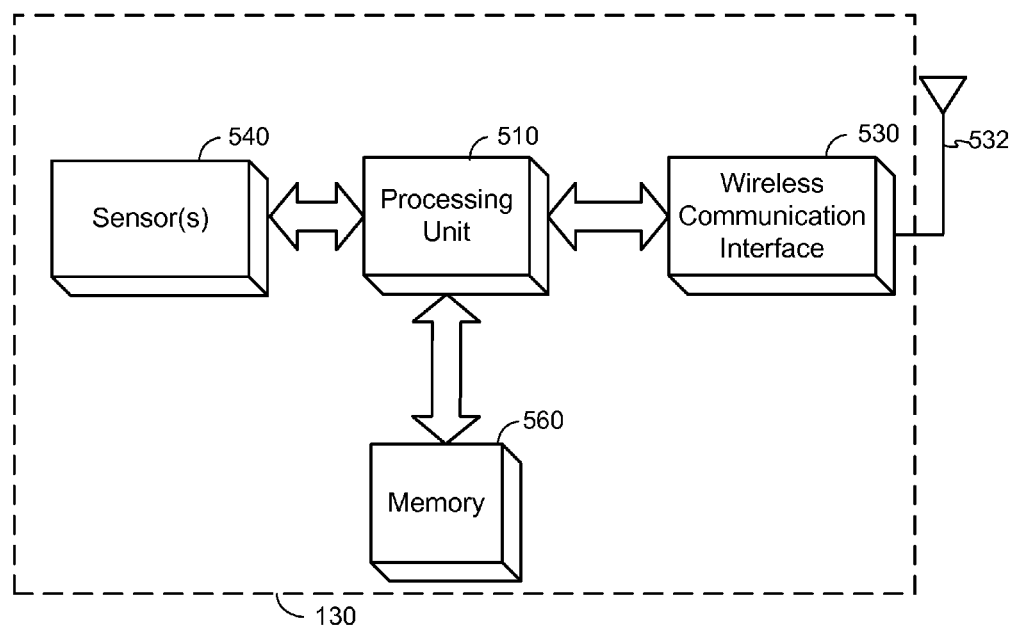
FIG. 5 is a simplified block diagram illustrating components of a transmitter unit, according to one embodiment.

Received data can be sent, via a bus, to a secure "island" 230. The secure island 230 can comprise a set of low-power components, including one or more routing components, at or near the entry point of the receiver unit 120 configured to securely route and/or process data received from the front-end module 210. These components can be implemented in hardware and/or software discrete from the components traditionally implemented in a mobile device (e.g., components as shown in FIG. 5). Additionally or alternatively, components of the secure island may be incorporated into and/or implemented by such traditional components, depending on desired functionality.

In some embodiments, as is shown in FIGS. 2A-2C, the secure island 230, application processor 240, and or other components may be part of a platform chipset 220, including "system on a chip" (SoC) and/or other multi-component integrated circuits. Example platform chipsets 220 can include ARM architecture CDMA and UMTS modem chipsets designated Mobile Station Modem (MSM), such as the Qualcomm® Snapdragon™ family of platform chipsets. In other embodiments, one or more of the components illustrated in FIGS. 2A and 2B as part of the platform chipset 220 may be distinct and/or implemented within other components. An example of such a variation is shown in FIG. 2C, which is described in more detail below.

Data from the bus slave 214 can be received into the secure island 230 via a bus master 232, which can relay the information to a parser 234 via a bus access manager (BAM) 233. The parser 234 can be configured to route data to different components of the secure island 230 and/or platform chipset 220 based on a determined routing identifier.

Received data packets can include headers, flags, and/or other indicators to indicate the component(s) to which data should be routed. FIG. 2B helps illustrate examples of how data may be routed. Some or all data received by the wireless front-end unit 212 can follow a primary data path 280 to the parser 234 via the bus slave 214, bus master 232, and BAM 233. From there, however, the data may be sent to different components depending on how the data is flagged. Most Bluetooth, WiFi, and/or other data received at the front-end module 210 can be routed from the parser 234 to an application processor 240 and memory 231 via respective application processor and memory data paths, 260 and 250. The application processor 240 can comprise a processing unit with one or more processing cores, capable of executing applications 244, wireless stack 242, and/or other software components and/or subsystems. Because the application processor 240 can function as the mobile device's primary processing unit, it can be relatively high in both processing power and power consumption.

On the other hand, sensor data (and/or information extracted therefrom) received from one or more transmitter units 130 can be flagged as such, and may be routed to a low-power processing unit 235 of the secure island 230 for processing via a low-power processing unit data path 270. (Data may also be sent to the memory 231.) The low-power processing unit 235 can comprise a processing core configured to process some or all data received by transmitter units 130. The low-power processing unit may further utilize bus master and/or sensors, 236 and 237 respectively. Here, the sensors 237 depict the functionality (typically implemented in software) of the low-power processing unit 235 that processes the sensor data, which can be tuned for specific processes and for very low power, thereby providing energy savings. The bus master 236 similarly depicts functionality (also typically implemented in software) of a bus manager that is contained into the low-power processing unit 235 and controlled by the sensors 237, as required for managing the data flow and information.

The memory 231 can comprise, at least in part, secure memory that may not be directly accessible to certain applications 244 or other functions performed by the application processor 240. In some embodiments, the memory 231 can store one or more encryption keys used to decrypt sensor data, as discussed in further detail below. This can include, for example, a One Time Programmable (OTP) memory that can store one or more predetermined encryption keys. When encryption keys are used, a timestamp may be written to the OTP regarding usage of the encryption key and/or number of times the key has been used.

Additionally or alternatively, the receiver unit 120 may include a biometric verification module (not shown), that may be used in for establishing an encryption key and/or for pairing a transmitter unit 130 with the receiver unit 120. The biometric verification module could include software and/or hardware means for obtaining biometric information, creating an encryption key based on the obtained biometric information, and/or verifying whether (and/or to what degree) newly-obtained biometric information matches stored biometric information. The biometric verification could include type of physiological and/or behavioral biometric input, including, for example, fingerprint, iris scan, signature, voice, and the like. An algorithm can be used to establish a unique encryption key based on features of the biometric data, and store the encryption key in the memory 231. As an example, a receiver unit 120 may have a biometric verification module with a fingerprint scanner (not shown) that can be used to obtain a user's fingerprint and establish an encryption key based on detected minutiae. Because the fingerprint is unique to the user, the encryption key, when based on unique features of the fingerprint, can be unique. In some embodiments, an application 244 executed by the application processor 240 may perform a setup by which the biometric verification is obtained. However, the establishment and storage of the encryption key may be done at a secure, device level. The device can then communicate to the application 244 that an encryption key has been successfully established.

Additionally or alternatively, biometric verification may be utilized when communicatively coupling (e.g., "pairing") a transmitter unit 130 to the receiver unit 120. As an example embodiment, a user 110 who wants to couple a transmitter unit 130 with a receiver unit may put the transmitter unit in a pairing mode. The receiver unit 120, when it detects the new transmitter unit 130 may then indicate to the user (e.g., via a display) that a new transmitter unit 130 has been detected, and ask the user 110 whether the user wants to couple the transmitter unit 130 to the receiver unit 120. If the user 110 selects "yes" (e.g., by selecting a corresponding button on a touchscreen display), but receiver unit 120 may then ask for fingerprint verification. Once the user provides the proper fingerprint (as determined by the biometric verification module—comparing the newly-obtained fingerprint with a stored fingerprint), the receiver unit 120 may then proceed to couple with the transmitter unit 130. Other types of processes may be used to require biometric verification for coupling transmitter units 130 to a receiver unit 120. Again, the biometric verification may be done at the device level to help ensure security. If an application needs to know whether biometric verification has been successful, the device can relay such information to the application layer. Biometric information (e.g., reference images, information regarding minutiae of a fingerprint, etc.) may be stored in the secure memory 231.

Routing data in the manner described in relation to FIGS. 2A and 2B can significantly increase power savings. In many applications, including health and medical applications, transmitter units 130 can operate all the time. Even when transmitter units 130 implement power-saving functions such as batching and/or compression, there can still be a significant amount of sensor data received at the front-end module 210 nearly all the time. If all this data were routed to the application processor 240 for processing, it would require the application processor 240 to be powered up nearly all the time, resulting in a large amount of power consumption and lower battery life for the receiver unit 120. However, because flagged sensor data is routed to the low-power processing unit 235 instead of sent to the application processor 240, such routing techniques can allow the application processor 240 to remain in low-power (e.g., "sleep") mode. Although the power savings can vary, depending on the application processor 240 and low-power processing unit 235 utilized and other factors, total power usage can be several times less than when sensor data is routed to an application processor 240.

FIG. 2C helps illustrate an example of how data may be routed in an alternate configuration. In this configuration, rather than include the parser 234 in the secure island 230, the parser 234 is located in the front-end module 210. As such, data following the primary data path 280 is split earlier on in the process (as compared with the configuration shown in FIG. 2B), although the data follows paths similar to the paths shown in FIG. 2B. That is, data for the application processor is routed along an application processor data path 260, and data destined for the memory 231 and low-power processing unit 235 is routed along corresponding memory data path 250 and low-power processing unit data path 270. As with the configuration shown in FIGS. 2A and 2B, the configuration shown in FIG. 2C can conserve power by routing received sensor data to the memory 231 and/or low-power processing unit 235 without involving the application processor 240.

Figure 3:
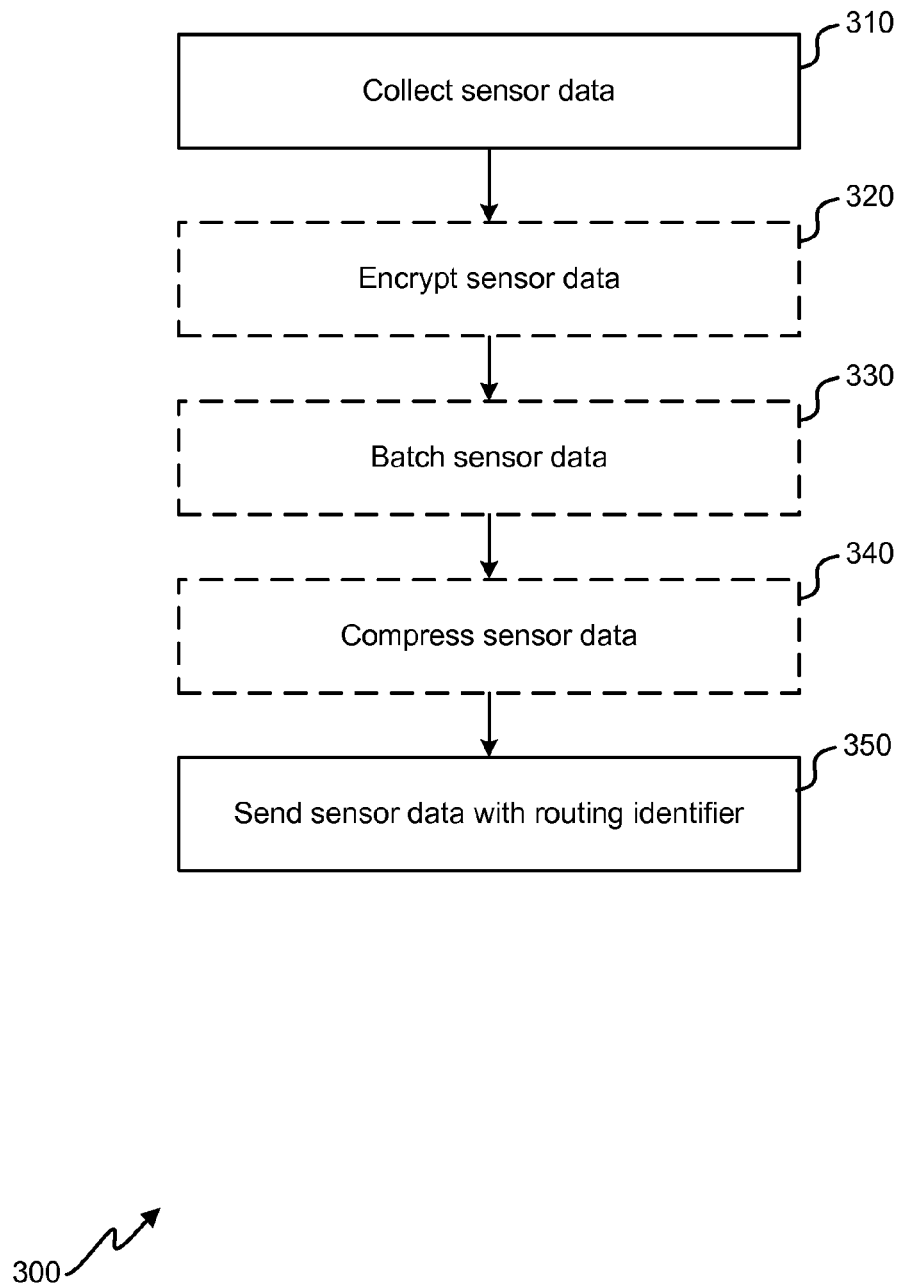
FIG. 3 is a flow diagram broadly illustrating a method of and transmitting information in a low-power wireless sensor interconnectivity system, according to one embodiment.

The power-saving techniques utilized herein not only can involve specialized components in the receiver unit 120, but also specialized functionality at the transmitter units 130, where the flagging of information for routing to the low-power processing unit 235 can originate. FIG. 3 is a flow diagram broadly illustrating a method 300 of collecting and transmitting information in a low-power wireless sensor interconnectivity system that can be executed by a transmitter unit 130 or other device, according to one embodiment.

Means for performing some or all of the blocks of the method 300 can be provided by the hardware and/or software of a transmitter unit 130. Details regarding such hardware and software components of an embodiment of a transmitter unit 130 are provided below with regard to FIG. 5. The blocks of the method 300 illustrated in FIG. 3 are provided as an example. A person of ordinary skill in the art will recognize that other embodiments may omit, add, substitute, and/or rearrange blocks, and/or make other variations on the method 300 shown.

The method 300 can begin at block 310, where sensor data is collected. Sensor data can include data from one or more sensors embedded in and/or communicatively coupled with the transmitter unit 130. The type of sensors can vary, depending on desired functionality. For health applications, sensors can include, for example, accelerometers, gyroscopes, altimeters, as well as sensors that can detect sound, pressure, heat, light, brainwaves, pulse, and the like.

Optionally, at block 320, the sensor data is encrypted. Here, the encryption may be performed by a proprietary encryption engine separate from any wireless encryption that may be provided when communicating data to the receiver unit 120. Thus, even if wireless data transfer to the receiver unit is intercepted by a listening device, and the wireless encryption is compromised, the encryption provided at block 320 would still protect the data. This supplementary encryption can therefore be used in embodiments in which additional security of sensitive information, such as medical information, is desired.

According to some embodiments, a private encryption key can be utilized in the encryption and set by an operator (e.g., the user 110, doctor, caregiver, etc.), or set using biometric identification and or other means as described above. The encryption key can take essentially take any degree of complexity, up to the highest level in use today. As indicated in further detail below, when encryption is utilized in the transmitter units 130 as is optionally shown in FIG. 3, corresponding decryption is utilized on the receiver unit 120.

In some embodiments, the private key may be manually changed by the operator or automatically changed in accordance with a security algorithm (e.g., cycling through private keys on a schedule). The change may be initiated by the receiver unit 120, which can send a message with the previously validated key to the transmitter unit 130. For its part, the transmitter unit 130 may also be equipped with an OTP memory which can store a predetermined number of keys, a time stamp of when the keys have been changed, and/or the number of key changes. The system could be such designed so that, based on the OTP state, it would control the access to the data process, eventually denying the unlawful client.

At block 330, sensor data can optionally be batched. That is, rather than transmitting sensor data as it is received, a transmitter unit 130 can bundle sensor data collected over a period of time and send it out as a single batch. Batching can reduce energy consumption by reducing the frequency of transmission of the sensor data.

Batching algorithms can vary, depending on desired functionality. Batches may be collected and transmitted, for example, based on certain schedules (e.g., time(s) of day, day(s) of the week, etc.), periods of time (e.g., a certain number of seconds, hours, days, etc.), triggering events (e.g., data requests from a receiver unit 120, detection of movement, receipt of data values at or above a certain threshold, etc.), and the like.

At block 340, the sensor data can optionally be compressed. Because transmission for transmitter units 130 is often a far greater power cost than processing, compressing sensor data can provide power savings. That is, the power cost of the additional processing power it takes to compress sensor data is usually less than the power savings of transmitting the compressed data (vs. transmitting uncompressed data). This can, of course, vary depending on the components used (e.g., processor and transmitter), compression rate, and other factors. When a transmitter unit 130 compresses the sensor data before transmission, a corresponding step is taken by the receiver unit 120 to decompress the sensor data.

Compression techniques can vary, depending on implementation, data type, and/or other factors. Lossy compression of certain data may be permitted in certain embodiments, while requiring lossless data of other data types. Audio of a heartbeat, for example, may be compressed via conversion into a lossy MPEG-2 Audio Layer III (MP3) file. In some embodiments, a transmitter unit 130 may employ specialized hardware to maximize efficiency when compressing sensor data.

At block 350, the sensor data is sent with the routing identifier. As previously indicated, the routing identifier can act as a flag to the receiver unit 120 to route sensor data to a low-power processing unit, such as the low-power processing unit 235 of FIGS. 2A-2C. The routing identifier may additionally or alternatively act as a flag to ensure the sensor data is routed only to particular secure elements within the receiver unit 120.

The routing identifier may be implemented in a variety of ways, depending on factors such as the wireless technology and/or protocols used. In one embodiment, the routing identifier can be embedded in a header of a data packet with a payload that includes the sensor data (which may be compressed, encrypted, and/or batched, as noted above).

The routing identifier can include a variety of information identifiable by the receiver unit 120 to route the received data to the correct components. Such information can include, for example and without limitation, a device identifier of the transmitter unit 130 and/or receiver unit 120, a pre-defined code, a certain protocol governing the format of the payload, and the like.

Figure 4:
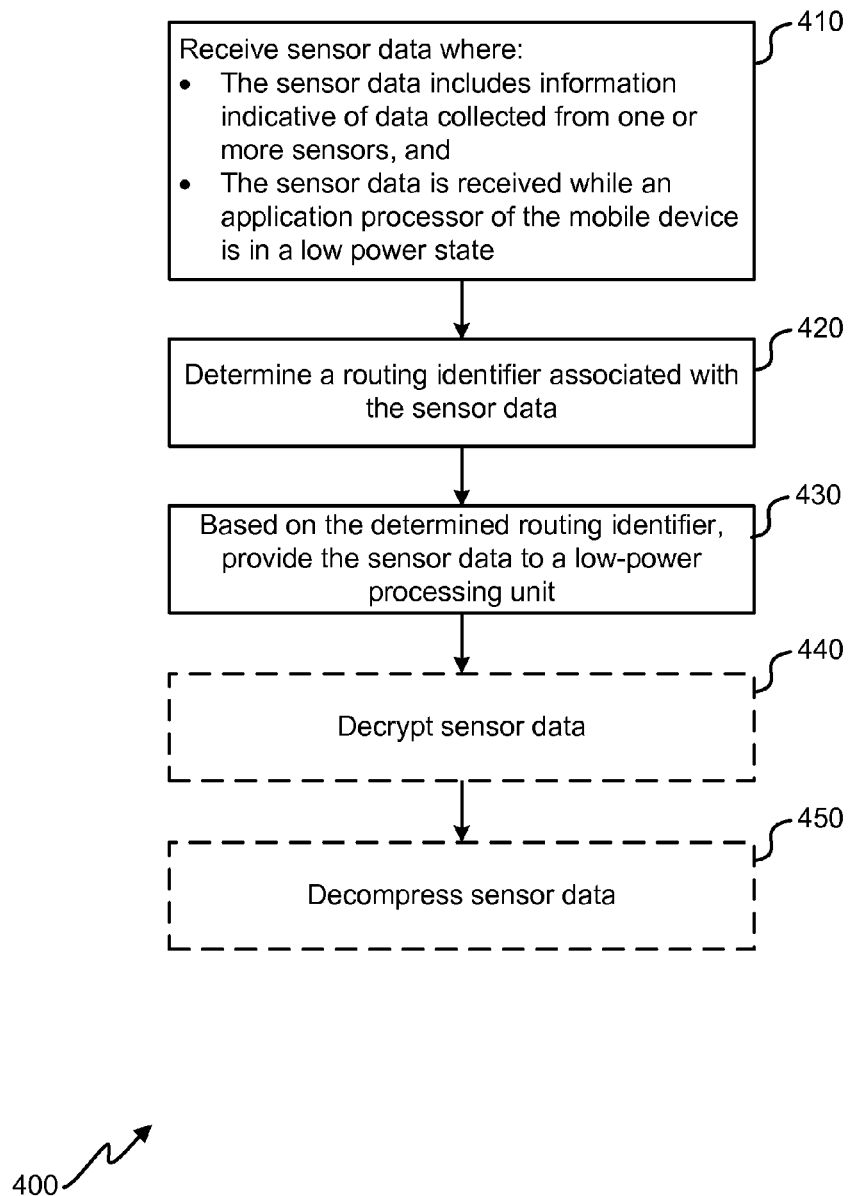
FIG. 4 is a flow diagram broadly illustrating a method of processing sensor data in a low-power wireless sensor interconnectivity system, according to one embodiment.

Power-saving techniques can be implemented on the device receiving the data as well. FIG. 4 is a flow diagram broadly illustrating a method 400 of processing sensor data in a low-power wireless sensor interconnectivity system that can be executed by a receiver unit 120 or other device, according to one embodiment.

Means for performing some or all of the blocks of the method 400 can be provided by the hardware and/or software of a receiver unit 120. Details regarding such hardware and software components of an embodiment of a receiver unit 120 are provided below with regard to FIG. 6. The blocks of method 400 illustrated in FIG. 4 are provided as an example. A person of ordinary skill in the art will recognize that other embodiments may omit, add, substitute, and/or rearrange blocks, and/or make other variations on the method 400 shown.

The method can begin at block 410, where sensor data is received. The sensor data can include information of data collected from one or more sensors, and the sensor data can be received while an application processor of the mobile device (e.g., receiver unit) is in a low-power state. As previously indicated, sensor data can include data from one or more sensors. Depending on desired functionality, the sensor data can include raw sensor readings and/or derivative data from a variety of sensor types.

Similar to batching discussed above in regard to FIG. 3, the transmittal and reception of data in a low-power wireless sensor interconnectivity system (comprising, for example, a receiver unit 120 and one or more transmitter units 130) can employ a variety of data techniques for power savings in wireless networks. Transmitter and receiver units can be synchronized, operating in a low-power or sleep mode when not transmitting or receiving, then "waking up" to send and/or receive data based on a schedule and/or periodic basis. Additionally or alternatively, transmitter and receiver units may wake up based on triggering events. In this context, however, "waking up" does not involve waking up the application processor from a low-power state. Instead, only components used for receipt and processing of the sensor data need to be woken up. Using the receiver unit 120 of FIGS. 2A and 2B as an example, only components in the front-end module 210 and secure island 230 need to be utilized. Thus, the application processor 240 can remain in a low-power state.

At block 420 a routing identifier associated with the sensor data is determined The routing identifier can be embedded within and/or otherwise communicated with the sensor data. As discussed above, the routing identifier may be included in a header of a data packet in which the sensor data is communicated.

At block 430 the sensor data is provided to a low-power processing unit, based on the determined routing identifier. The low-power processing unit can be, for example, a processing unit, other than the application processor, that can process the sensor data. As illustrated in FIGS. 2A-2C, a parser 234 may route the data to the low-power processing unit 235 and/or the memory 231 without awaking the application processor. The low-power processing unit and the application processor may both be part of a platform chipset. According to some embodiments, power savings gained by using the low-power processing can be several times greater than if unit rather than the application processor, although this can vary depending on relative power consumption.

Optionally, at block 440, the sensor data may be decrypted. As previously discussed, transmitter units 130 may encrypt sensor data to provide an additional layer of security, which may be useful in a variety of applications. In such instances, the sensor data can be correspondingly decrypted once received. And, as indicated above, decryption can occur at the device or application layer, separate from any additional wireless encryption that may be utilized. In some embodiments, the low-power processing unit (e.g., the low-power processing unit 235 of FIGS. 2A-2C) can perform the decryption. Additionally or alternatively, a private key used in decryption can be stored in a secure memory (such as the memory 231 of the secure island 230 shown in FIGS. 2A-2C, for example).

At block 450, the sensor data may optionally be decompressed. Again, if sensor data is compress prior to transmission, it can be correspondingly decompressed after it is received. In some embodiments, a receiver unit may employ specialized hardware to maximize efficiency when decompressing sensor data. In some embodiments, the low-power processing unit (e.g., the low-power processing unit 235 of FIGS. 2A-2C) can perform the decompression.

FIG. 5 is a simplified block diagram illustrating components of a transmitter unit 130, according to one embodiment, which can implement the sensor data collection and flagging techniques discussed herein, including the method illustrated in FIG. 3. It should be noted that FIG. 5 is meant only to provide a generalized illustration of various components, any or all of which may be utilized as appropriate. Moreover, system elements may be implemented in a relatively separated or relatively more integrated manner. Additionally or alternatively, some or all of the components shown in FIG. 5 can be utilized in another device communicatively coupled with the transmitter unit 130.

The hardware elements may include a processing unit 510, including without limitation one or more general-purpose processors and/or one or more special-purpose processors (such as a programmable microprocessor, microcontroller, application-specific integrated circuit (ASIC), programmable logic (e.g., FPGA), and the like), and/or other processing structure or means, which can be configured to perform one or more of the methods described herein, including the illustrated in FIG. 3.

The processing unit 510 may be in communication with a memory 560. The memory 560 can include, without limitation, a solid-state storage device, such as a random access memory ("RAM"), and/or a read-only memory ("ROM"), which can be programmable, flash-updateable, and/or the like. Additionally or alternatively, a processing unit 510 may incorporate on-board memory to perform some or all of the functions described herein. Memory can be used to store motion sensor data, logic for execution by the processing unit 510, and/or other information described herein.

The transmitter unit 130 can further include one or more sensors 540. Such sensors can include, without limitation, one or more accelerometer(s), gyroscope(s), camera(s), magnetometer(s), altimeter(s), microphone(s), proximity sensor(s), light sensor(s), and/or other sensors configured to collect data regarding light, heat, pressure, sound, electric and/or magnetic fields, movement, orientation, and the like. In some embodiments, as shown in FIG. 5, sensor(s) 540 can be incorporated into the transmitter unit 130. Additionally or alternatively, sensor(s) 540 may be disposed outside of the transmitter unit 130, communicatively coupled with the processing unit 510 via, for example, a wired or wireless data connection.

The wireless communication interface 530 can include an infrared communication device, a wireless communication device, and/or a chipset, which may employ one or more wireless technologies, such as Bluetooth™, ZigBee®, and/or other technologies as previously described. As indicated herein, the wireless technology may employ encryption and/or other data manipulation that may be separate from any encryption performed by the processing unit 510. The wireless communication interface 530 may permit data to be exchanged with a receiver unit 120, such as the receiver unit illustrated in FIGS. 1-2C, network, or other device, such as the mobile device illustrated below in FIG. 6. The communication can be carried out via one or more wireless communication antenna(s) 532.

The components of the transmitter unit 130 shown in FIG. 5 are provided as a simplified example. Hardware and/or software of a transmitter unit 130 can vary, depending on application, sensor(s) 540, and/or other factors. In some embodiments, components may be added, omitted, rearranged, combined, or separated. A person of ordinary skill in the art will recognize that additional or alternative features may be implemented, including the features of a mobile device as described below with regard to FIG. 6.

Figure 6:
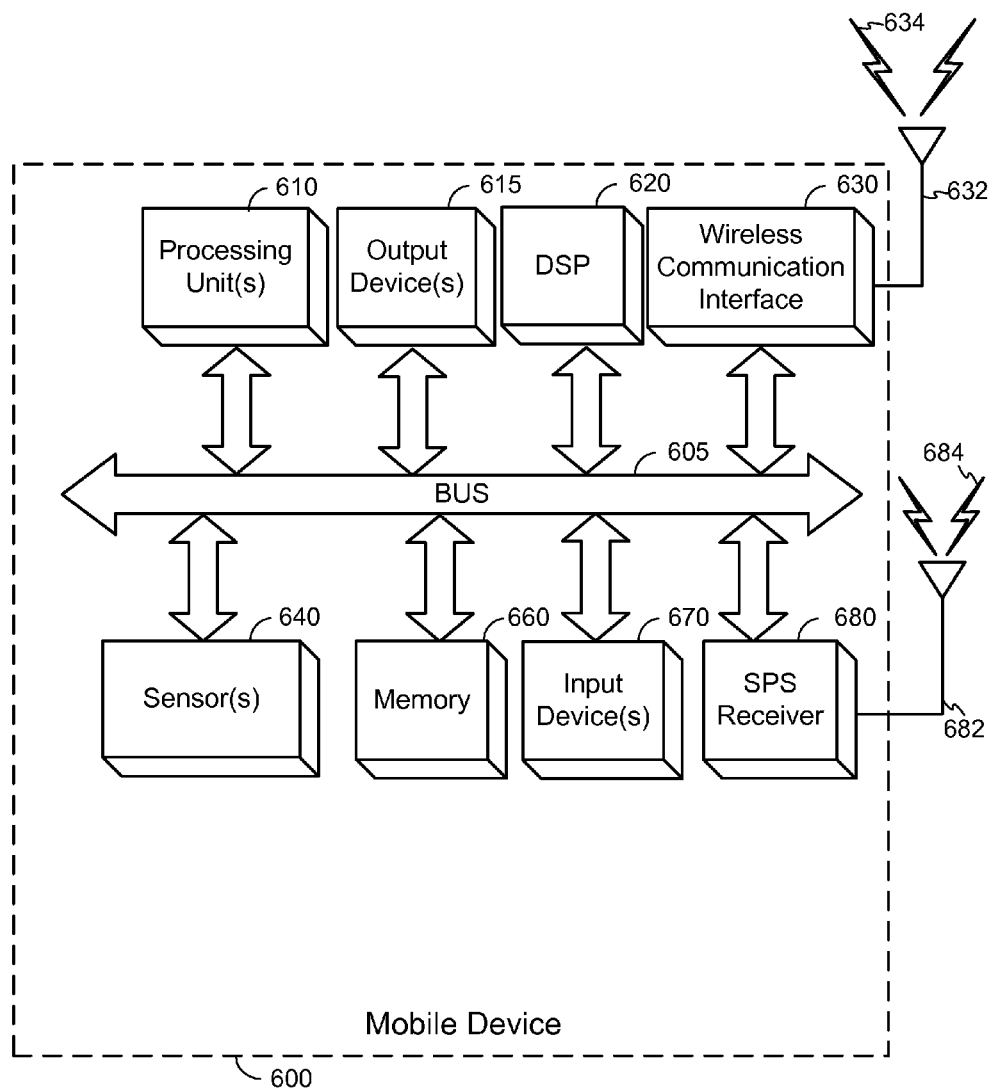
FIG. 6 illustrates components of an embodiment of a mobile device, which can implement the functions of a receiver unit as described herein.

FIG. 6 is a simplified block diagram illustrating an embodiment of a mobile device 600, which can perform the features of a receiver unit 120. Although not illustrated explicitly here, components of the receiver unit 120 of FIGS. 2A-2C can be implemented using hardware and/or software components of the mobile device 600 shown in FIG. 6. Additionally or alternatively, a mobile device may be communicatively connected with a separate receiver unit 120. It should be noted that FIG. 6 is meant only to provide a generalized illustration of various components, any or all of which may be utilized as appropriate. Moreover, system elements may be implemented in a relatively separated or relatively more integrated manner. Additionally or alternatively, some or all of the components shown in FIG. 6 can be utilized in another computing device communicatively coupled with the mobile device 600.

The mobile device 600 is shown comprising hardware elements that can be electrically coupled via a bus 605 (or may otherwise be in communication, as appropriate). The bus 605 and/or components connected therewith can, for example, comprise and/or perform the functions of the bus slave 214, bus master 232, and/or BAM 233 of FIGS. 2A-2C. In some embodiments, the bus may comprise a SLIMbus.

The hardware elements connected to the bus 605 may include a processing unit(s) 610 which can include without limitation one or more general-purpose processors, one or more special-purpose processors (such as digital signal processors (DSPs), graphics acceleration processors, application specific integrated circuits (ASICs), and/or the like), and/or other processing structure or means, which can be configured to perform one or more of the methods described herein, including the method illustrated in FIG. 4. The processing unit(s) 610 may comprise and/or perform the functions of the application processor 240, low-power processing unit 235, and/or other components of the platform chipset 220 illustrated in FIGS. 2A-2C. As shown in FIG. 6, some embodiments may have a separate DSP 620, depending on desired functionality. The mobile device 600 also can include one or more input devices 670, which can include without limitation one or more camera(s), a touch screen, a touch pad, microphone, button(s), dial(s), switch(es), and/or the like; and one or more output devices 615, which can include without limitation a display, light emitting diode (LED), speakers, and/or the like.

Similar to the transmitter unit 130 of FIG. 5, the mobile device 600 might also include a wireless communication interface 630, which can include without limitation a modem, a network card, an infrared communication device, a wireless communication device, and/or a chipset (such as a Bluetooth™ device, ZigBee® device, an IEEE 602.11 device, an IEEE 602.15.4 device, a WiFi device, a WiMax device, cellular communication facilities, etc.), and/or the like, including previously-discussed wireless technologies. The wireless communication interface 630 may permit data to be exchanged with one or more transmitter units 130 as described herein. The mobile device may also communicate with networks, wireless access points, computer systems, and/or other electronic devices. The communication can be carried out via one or more wireless communication antenna(s) 632 that send and/or receive wireless signals 634. The wireless communication interface 630 may comprise and/or perform the functions of the wireless front-end 212 and/or other components of the front-end modules 210 illustrated in FIGS. 2A-2C.

Depending on desired functionality, the wireless communication interface 630 can include separate transceivers to communicate with base transceiver stations (e.g., base transceiver stations of a cellular network) and access points. These different data networks can include an OFDMA and/or other type of network.

The mobile device 600 can further include sensor(s) 640. Such sensors can include, without limitation, one or more accelerometer(s), gyroscope(s), camera(s), magnetometer(s), altimeter(s), microphone(s), proximity sensor(s), light sensor(s), and the like. In addition to sensor data received from one or more transmitter units 130, techniques described herein may further utilize sensor data from the sensor(s) 640 of a mobile device 600

Embodiments of the mobile device may also include a Satellite Positioning System (SPS) receiver 680 (such as Global Positioning System (GPS), for example) capable of receiving signals 684 from one or more SPS satellites using an SPS antenna 682. It can be noted that an SPS may include any combination of one or more global and/or regional navigation satellite systems and/or augmentation systems, and SPS signals may include SPS, SPS-like, and/or other signals associated with such one or more SPS. Such positioning can be utilized to complement and/or incorporate the techniques described herein. For example, a mobile device 600 may be configured to transmit information to a remote system based on triggering event (e.g., transmit information to a remote emergency medical system based on sensor data indicative of a life-threatening emergency). The location of the mobile device 600, as indicated by the SPS receiver 680 could be indicated in the transmitted information.

The mobile device 600 may further include and/or be in communication with a memory 660. The memory 660 can include, without limitation, local and/or network accessible storage, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data structures and/or other memory utilized by the techniques described herein. Additionally or alternatively, data structures described herein can be implemented by a cache or other local memory of a DSP 620 or processing unit(s) 610.

The memory 660 of the mobile device 600 also can comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more procedures described with respect to the method(s) discussed above, such as the method illustrated in FIG. 4, might be implemented as code and/or instructions executable by the mobile device 600 (and/or processing unit(s) 610 within a mobile device 600) and/or stored on a non-transitory and/or machine-readable storage medium (e.g., a "computer-readable storage medium," a "machine-readable storage medium," etc.), such as memory 660. In an aspect, then, such code and/or instructions can be used to configure and/or adapt a general purpose processor (or other device) to perform one or more operations in accordance with the described methods.

It may be further noted that such non-transitory machine-readable media for performing one or more of the methods described herein may be stored—collectively or separately—in the cache and/or other on-board memory of different hardware components as shown in FIGS. 2A, 2B, 2C, 5, and 6.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

What is claimed is:

1. A method of processing sensor data in a low-power wireless sensor interconnectivity system, the method comprising:
    receiving sensor data with a wireless communications interface of a mobile device, wherein:
        the sensor data includes information indicative of data collected from one or more sensors,
        the mobile device includes a secure island comprising components, including one or more routing components, configured to securely route and process data received with the wireless communications interface,
        the mobile device includes an application processor separate from the secure island and a low-power processing unit composing at least a part of the secure island, and
        the sensor data is received while the application processor is in a low-power state;
    determining a routing identifier associated with the sensor data; and
    based on the determined routing identifier, providing the sensor data to the low-power processing unit using the one or more routing components of the secure island.

2. The method of claim 1, further comprising decrypting the sensor data with the low-power processing unit using an encryption key.

3. The method of claim 2, further comprising establishing the encryption key using biometric verification.

4. The method of claim 3, wherein the biometric verification comprises using a scan of a fingerprint.

5. The method of claim 2, wherein the encryption key is one of a plurality of predetermined encryption keys stored in a One Time Programmable (OTP) memory of the mobile device.

6. The method of claim 2, further comprising writing a time stamp to an OTP memory regarding usage of the encryption key.

7. The method of claim 1, further comprising decompressing the sensor data with the low-power processing unit.

8. The method of claim 1, further comprising sending the sensor data to a cloud-based decision support system (DSS).

9. An apparatus in a low-power wireless sensor interconnectivity system, the apparatus comprising:
    a secure island comprising components, including one or more routing components, configured to securely route and process data received with the wireless communications interface;
    an application processor separate from the secure island;
    a low-power processing unit composing at least a part of the secure island;
    a wireless communication interface communicatively coupled with the application processor and the low-power processing unit, the wireless communication interface configured to receive, while the application processor is in a low-power state, sensor data including information indicative of data collected from one or more sensors; and
    one or more routing components communicatively coupled with the wireless communication interface and the low-power processing unit, the one or more routing components configured to:
        determine a routing identifier associated with the sensor data; and
        provide the sensor data to the low-power processing unit, based on the determined routing identifier, using the one or more routing components of the secure island.

10. The apparatus of claim 9, wherein the low-power processing unit is configured to decrypt the sensor data using an encryption key.

11. The apparatus of claim 10, further comprising a biometric verification module configured to establish the encryption key using biometric verification.

12. The apparatus of claim 11, wherein the biometric verification module comprises a fingerprint scanner.

13. The apparatus of claim 10, wherein the encryption key is one of a plurality of predetermined encryption keys, the apparatus further comprising a One Time Programmable (OTP) memory of the apparatus configured to store the plurality of predetermined encryption keys.

14. The apparatus of claim 10, wherein an OTP memory is configured to store a time stamp regarding usage of the encryption key.

15. The apparatus of claim 9, wherein the low-power processing unit is configured to decompress the sensor data.

16. The apparatus of claim 9, wherein either or both the low-power processing unit or the application processor is configured to send the sensor data to a cloud-based decision support system (DSS) via the wireless communication interface.

17. A mobile device comprising:
    means for receiving sensor data, wherein:
        the means for receiving sensor data includes means for receiving information indicative of data collected from one or more sensors, the mobile device includes secure routing and processing means, configured to securely route and process data received with the means for receiving sensor data, and the means for receiving sensor data includes means for receiving the sensor data while an application processor of the mobile device is in a low-power state, the application processor being separate from the secure routing and processing means;

means for determining a routing identifier associated with the sensor data; and means for providing the sensor data to a low-power processing unit based on the determined routing identifier, wherein the lower-power processing unit composes at least a part of the secure routing and processing means, and the secure routing and processing means compose at least a part of the means for providing the sensor data to the low-power processing unit.

18. The mobile device of claim 17, further comprising means for decrypting the sensor data using an encryption key while the application processor of the mobile device is in the low-power state.

19. The mobile device of claim 18, further comprising means for establishing the encryption key using biometric verification.

20. The mobile device of claim 19, wherein the means for establishing the encryption key using biometric verification comprises means for using a scan of a fingerprint.

21. The mobile device of claim 18, wherein the encryption key is one of a plurality of predetermined encryption keys, further comprising means for storing the plurality of predetermined encryption keys in a One Time Programmable (OTP) memory of the mobile device.

22. The mobile device of claim 18 further comprising means for writing a time stamp to an OTP memory regarding usage of the encryption key.

23. The mobile device of claim 17, further comprising means for decompressing the sensor data while the application processor of the mobile device is in the low-power state.

24. The mobile device of claim 17, further comprising means for sending the sensor data to a cloud-based decision support system (DSS).

25. A non-transitory computer-readable medium comprising instructions for processing sensor data in a low-power wireless sensor interconnectivity system, the instructions including code for causing one or more components of a mobile device to perform functions including:

receiving sensor data with a wireless communications interface of the mobile device, wherein:

the code for receiving sensor data includes code for receiving information indicative of data collected from one or more sensors, the mobile device includes a secure island comprising components, including one or more routing components, configured to securely route and process data received with the wireless communications interface, and the code for receiving sensor data includes code for receiving the sensor data while an application processor of the mobile device, separate from the secure island, is in a low-power state;

determining a routing identifier associated with the sensor data; and providing the sensor data to a low-power processing unit composing at least a part of the secure island, based on the determined routing identifier, using the one or more routing components of the secure island.

26. The computer-readable medium of claim 25, further comprising code for decrypting the sensor data using an encryption key while the application processor of the mobile device is in the low-power state.

27. The computer-readable medium of claim 26, further comprising code for establishing the encryption key using biometric verification.

28. The computer-readable medium of claim 26, wherein the encryption key is one of a plurality of predetermined encryption keys, further comprising c for storing the plurality of predetermined encryption keys in a One Time Programmable (OTP) memory of the mobile device.

29. The computer-readable medium of claim 26, further comprising code for writing a time stamp to an OTP memory regarding usage of the encryption key.

30. The computer-readable medium of claim 25, further comprising code for sending the sensor data to a cloud-based decision support system (DSS).

* * * * *